United States Patent [19]

Lesher et al.

[11] 4,375,467

[45] Mar. 1, 1983

[54] 5-(PYRIDINYL)-1H-PYRAZOLO[3,4-b] PYRIDINES AND THEIR CARDIOTONIC USE

[75] Inventors: George Y. Lesher, Schodack; Monte D. Gruett, East Greenbush, both of N.Y.

[73] Assignee: Sterling Drug Inc., New York, N.Y.

[21] Appl. No.: 305,913

[22] Filed: Sep. 28, 1981

[51] Int. Cl.$^3$ .................... C07D 487/04; A61K 31/44
[52] U.S. Cl. ..................................... 424/263; 546/119
[58] Field of Search ................. 546/119; 424/263, 256

[56] References Cited

U.S. PATENT DOCUMENTS 3,403,158  9/1968  Markillie ............................. 546/119

FOREIGN PATENT DOCUMENTS 2317230  10/1973  Fed. Rep. of Germany .

OTHER PUBLICATIONS

Chemical Abstracts 80: 27117g (1974).

Chemical Abstracts vol. 87, item 39, 357t, 1977.
Balicki, Roman; Kaczmarek, Lukasz; Nantka-Namirski, Pawel (Inst. Org. Chem., Pol. Acad. Sci., Warsaw, Pol.) Acta Pol. pharm. 1976, 33(3), 289–93 (Pol.)and English Translation.

*Primary Examiner*—Norma S. Milestone
*Attorney, Agent, or Firm*—Robert K. Bair; B. Woodrow Wyatt; Paul E. Dupont

[57] ABSTRACT

1-R-3-R'-5-PY-1H-pyrazolo[3,4-b] pyridines (I) or acid-addition salts thereof, which are useful as cardiotonics, are prepared by reacting a α-PY-β-dimethylamino-acrolein with 5-amino-1-R-3-R'-1H-pyrazole, where R is lower-alkyl or lower-hydroxyalkyl, R' is hydrogen or lower-alkyl, and PY is 4- or 3-pyridinyl or 4- or 3-pyridinyl having one or two lower-alkyl substituents. Also shown are cardiotonic compositions and method for increasing cardiac contractility using said compounds (I) or pharmaceutically acceptable acid-addition salts thereof.

8 Claims, No Drawings

5-(PYRIDINYL)-1H-PYRAZOLO[3,4-b] PYRIDINES AND THEIR CARDIOTONIC USE

CROSS REFERENCE TO RELATED APPLICATIONS

Lesher and Gruett application Ser. No. 132,227, filed Mar. 17, 1980 and now U.S. Pat. No. 4,264,603, issued Apr. 28, 1981, shows 1-R-5-(pyridinyl)-1H-pyrazolo[3,4-b]pyridin-3-amines as cardiotonics and their preparation by reacting a 2-halo-5-(pyridinyl)-nicotinonitrile with a 1-R-hydrazine where R is, inter alia, hydrogen, lower-alkyl and lower-hydroxyalkyl.

BACKGROUND OF THE INVENTION

1. Field of the Invention

This invention relates to 5-(pyridinyl)-1H-pyrazolo[3,4-b]pyridines, their preparation and their use as cardiotonics.

2. Description of the Prior Art

Chemical Abstracts Vol. 87, item 39,357t, 1977, reads as follows:

"Dipyridyls. VII. Reaction of β-ketoaldehydes with cyanoacetic acid hydrazide. Balicki, Roman; Kaczmarek, Lukasz; Nantka-Namirski, Pawel (Inst. Org. Chem., Pol. Acad. Sci., Warsaw, Pol.). Acta Pol. Pharm. 1976, 33(3), 289-93 (Pol). RCOCH$_2$CHO (R=Me, Ph, 3- and 4-pyridyl, and

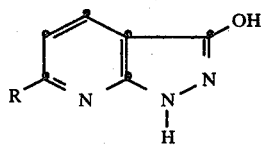

6-methyl-3-pyridyl) condensed in an alk. medium with NCCH$_2$CONHNH$_2$ (I) to give the pyrazolopyridines II. II were also obtained when 5-amino-3-pyrazolone was used instead of I. II (R=3- and 4-pyridyl) were also prepd. in the reaction of Me 6-(3- and 4-pyridyl)-2-chloronicotinates or 6-(3- and 4-pyridyl)-2-chloro-3-cyanopyridines with 80% NH$_2$NH$_2$.H$_2$O."

The original article (p. 291) shows that the compounds of formula II (supra) can also exist in tautomeric 1,2-dihydro-6-R-2H-pyrazolo[3,4-b]pyridin-3-one form.

SUMMARY OF THE INVENTION

In a composition of matter aspect, the invention relates to 1-R-3-R'-5-PY-1H-pyrazolo[3,4-b]pyridines or acid-addition salt thereof, where R, R' and PY are defined hereinbelow, which are useful as cardiotonic agents.

The invention in a process aspect comprises reacting α-PY-β-dimethylaminoacrolein with 5-amino-1-R-3-R'-1H-pyrazole to produce a 1-R-3-R'-5-PY-1H-pyrazolo[3,4-b]-pyridine.

A composition aspect of the invention relates to a cardiotonic composition for increasing cardiac contractility in a patient, said composition comprising a pharmaceutically acceptable carrier and, as the active ingredient thereof, a cardiotonically effective amount of 1-R-3-R'-5-PY-1H-pyrazolo[3,4-b]pyridine or pharmaceutically acceptable acid-addition salt thereof.

In a method aspect, the invention relates to a method for increasing cardiac contractility in a patient requiring such treatment which comprises the administration of a medicament comprising a pharmaceutically acceptable carrier and, as the active component thereof, a cardiotonically effective amount of 1-R-3-R'-5-PY-1H-pyrazolo[3,4-b]pyridine or pharmaceutically acceptable acid-addition salt thereof.

DETAILED DESCRIPTION OF PREFERRED EMBODIMENTS

In a composition of matter aspect the invention resides in a 1-R-3-R'-5-PY-1H-pyrazolo[3,4-b]pyridine having formula I

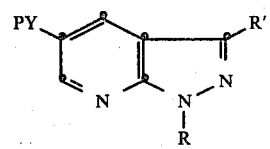

where R is lower-alkyl or lower-hydroxyalkyl, R' is hydrogen or lower-alkyl, and PY is 4- or 3-pyridinyl or 4- or 3- pyridinyl having one or two lower-alkyl substituents, or acid-addition salt thereof. The compounds of formula I are useful as cardiotonic agents, as determined by standard pharmacological evaluation procedures. Preferred embodiments are those of formula I where PY is 4-pyridinyl or 3-pyridinyl, R is methyl, ethyl or 2-hydroxyethyl and R' is hydrogen or methyl. A particularly preferred embodiment is the compound of formula I where R is 2-hydroxyethyl, R' is hydrogen and PY is 4-pyridinyl or acid-addition salt thereof.

In a process aspect the invention resides in the process of producing the 1-R-3-R'-5-PY-1H-pyrazolo[3,4-b]pyridine of formula I which comprises reacting α-PY-β-dimethylaminoacrolein with 5-amino-1-R-3-R'-1H-pyrazole, where PY, R and R' have the meanings given above for the compound of formula I. Preferred embodiments of this process are those which produce the above-said preferred composition embodiments of formula I preferably by heating α-(4- or 3-pyridinyl)-β-dimethylaminoacrolein with 5-amino-1-(methyl, ethyl or 2-hydroxyethyl)-1H-pyrazole in acetic acid.

A composition aspect of the invention resides in a cardiotonic composition for increasing cardiac contractility, said composition comprising a pharmaceutically acceptable carrier and, as the active component thereof, a cardiotonically effective amount of 1-R-3-R'-5-PY-1H-pyrazolo[3,4-[pyridine of formula I, where R, R' and PY are each defined as in formula I, or pharmaceutically acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient a cardiotonically effective amount of 1-R-3-R'-5-PY-1H-pyrazolo[3,4-b]pyridine of formula I where PY, R and R' are defined as in formula I, or pharmaceutically acceptable acid-addition salt thereof. Preferred embodiments of this method aspect are those using the preferred cardiotonics of formula I noted above.

The term "lower-alkyl" as used herein, e.g., as one of the meanings for R or R' or as a substituent for PY in formula I, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., for one of the meanings for R in formula I, means hydroxyalkyl radicals having from two to four carbon atoms which can be arranged as straight or branched chains and at least two carbon atoms of which separate hydroxy and the 1-ring nitrogen atom of the pyrazolo[3,4-b]pyridine ring, illustrated by 2-hydroxyethyl, 3-hydroxypropyl, 2-hydroxy-1-methylethyl, 4-hydroxybutyl, 2-hydroxy-2-methylethyl, 2-hydroxy-2-methylpropyl, 3-hydroxy-3-methylpropyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically acceptable salts within the scope of the invention are those derived from mineral acids such as hydrochloric acid, hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds (I) are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 1-R-3-R'-5-PY-1H-pyrazolo[3,4-b]pyridine (I) by reacting α-PY-β-dimethylaminoacrolein with 5-amino-1-R-3-R'-1H-pyrazole is carried out by heating the reactants in a suitable solvent at about 50° C. to 150° C., preferably about 80° C. to 120° C., where R, R' and PY have the meanings given above for formula I, preferably where PY is 4- or 3-pyridinyl, R is methyl, ethyl or 2-hydroxyethyl and R' is hydrogen or methyl. The reaction is preferably run by heating the reactants in acetic acid. Other suitable solvents include propionic acid, a lower-alkanol, e.g., ethanol or isopropyl alcohol preferably containing an acid such as hydrogen chloride, dimethylformamide, and the like.

The intermediate α-PY-β-dimethylaminoacroleins and 5-amino-1-R-3-R'-1H-pyrazoles are known or can be prepared by known methods. The α-PY-β-dimethylaminoacroleins are shown in U.S. Pat. Nos. 4,004,012 and 4,072,746. Illustrative references for 5-amino-1-R-3-R'-1H-pyrazoles are: U.S. Pat. No. 2,989,537; C.A. 63, 14871a (1965); C.A. 69, 96,710e (1968); C.A. 70, 11,624c (1969); and, C.A. 74, 13,057b (1971).

The following examples will further illustrate the invention without, however, limiting it thereto.

EXAMPLE 1

1-(2-Hydroxyethyl)-5-(4-pyridinyl)-1H-pyrazolo[3,4-b]pyridine, alternatively named 5-(4-pyridinyl)-1H-pyrazolo[3,4-b]pyridine-1-ethanol—A solution containing 63.4 g. of α(4-pyridinyl)-β-dimethylaminoacrolein, 38 g. of 5-amino-1-(2-hydroxyethyl)-1H-pyrazole and 500 ml. of acetic acid was heated with stirring on a steam bath for twenty-four hours, allowed to cool and stand at room temperature overnight. The dark red solution was evaporated in vacuo to leave a viscous red residual material which was dissolved in about 850 ml. of water. The aqueous solution was made basic to a pH of 8.5 with concentrated ammonium hydroxide (about 40 ml. required) to produce a heavier oily layer. The oily layer was extracted with 500 ml. of n-butanol and then successively with three 250 ml. portions of n-butanol. The combined n-butanol extracts were evaporated in vacuo and the remaining residue was dissolved in 50:50 (v:v) of isopropyl alcohol:ethyl acetate. The solution was passed through a column (13 cm.×16 cm.) packed under the same solvent combination with silica gel and eluted with 50:50 (v:v) isopropyl alcohol:ethyl acetate (about 16 liters). The eluates were combined and evaporated in vacuo to yield as a red viscous liquid 72.7 g. of crude 1-(2-acetoxyethyl)-5-(4-pyridinyl)-1H-pyrazolo[3,4-b]pyridine. Purification of a 10.7 g. sample of this crude product is shown below in Example 2. Conversion of 61 g. of said 1-(2-acetoxyethyl) compound to the corresponding 1-(2-hydroxyethyl) product is described in the following paragraph.

A solution containing 61 g. of said crude 1-(2-acetoxyethyl)-5-(4-pyridinyl)-1H-pyrazolo[3,4-b]pyridine and 610 ml. of 1 N aqueous hydrochloric acid was heated on a steam bath for twenty-two hours and then allowed to cool to room temperature. The red solution was filtered through a sintered glass funnel and the filtrate was made alkaline to a pH of 8 with saturated aqueous potassium carbonate solution (about 85 ml. required) and then cooled in an ice bath. The resulting copious pale yellow precipitate was collected by filtration, sucked as dry as possible, washed with a small amount of fresh cold water and again sucked as dry as possible. The damp solid was recrystallized from 160 ml. of acetonitrile, also using decolorizing charcoal, and dried in a vacuum oven at 90° C. to yield 19.2 g. of 1-(2-hydroxyethyl)-5-(4-pyridinyl)-1H-pyrazolo[3,4-b]pyridine, m.p. 153°–154° C. The above acetonitrile filtrate from the recrystallization was evaporated in vacuo to leave, as a light tan solid, another 13.2 g. of said product. A third crop of 12.9 g. of product was obtained by extracting the aqueous filtrates from above with three 250 ml. portions of methylene dichloride, combining the extracts, drying them over anhydrous magnesium sulfate, filtering of the drying agent and evaporating the filtrate to dryness in vacuo.

Acid-addition salts of 1-(2-hydroxyethyl)-5-(4-pyridinyl)-1H-pyrazolo[3,4-b]pyridine are conveniently prepared by adding to a mixture of 5 g. of 1-(2-hydroxyethyl)-5-(4-pyridinyl)-1H-pyrazolo[3,4-b]pyridine in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(2-hydroxyethyl)-5-(4-pyridinyl)-1H-pyrazolo[3,4-b]pyridine and the appropriate acid, e.g., lactic acid or hydrochloric acid, to prepare respectively the monolactate or monohydrochloride salt in aqueous solution.

EXAMPLE 2

1-(2-Acetoxyethyl)-5-(4-pyridinyl)-1H-pyrazolo[3,4-b]pyridine—Purification of a 10.7 g. sample of the crude 1-(2-acetoxyethyl)-5-(4-pyridinyl)-1H-pyrazolo[3,4-b]pyridine of Example 1 was achieved by dissolving the sample in 40 ml. of ethyl acetate and passing the solution by high pressure liquid chromatography through two columns (5.5 cm. by 30 cm.) of silica gel (350 g. each column) which had been previously washed and equilibrated with ethyl acetate: isopropyl alcohol (85:15 v/v) and then the columns were eluted with the same solvent combination. The eluant containing the product was evaporated in vacuo at 90° C. to effect complete removal of solvent. There was obtained 8.3 g. of an amber-colored, viscous liquid residue which was extracted several times with small portions of ether, the extracts combined, filtered and evaporated in vacuo to remove the ether, thereby leaving, as a viscous liquid, 6.4 g. of 1-(2-acetoxyethyl)-5-(4-pyridinyl)-1H-pyrazolo[3,4-b]pyridine.

Following the procedure described in Example 1 but using in place of α-(4-pyridinyl)-β-dimethylaminoacrolein and 5-amino-1-(2-hydroxyethyl)-1H-pyrazole molar equivalent quantities respectively of α-PY-β-dimethylaminoacrolein and 5-amino-1-R-3-R'-1H-pyrazole, it is contemplated that the corresponding 1-R-3-R'-5-PY-1H-pyrazolo[3,4-b]pyridines of Examples 3–16 can be obtained.

3. 1-(2-Hydroxyethyl)-5-(3-pyridinyl)-1H-pyrazolo[3,4-b]pyridine, using α-(3-pyridinyl)-β-dimethylaminoacrolein and 5-amino-1-(2-hydroxyethyl)-1H-pyrazole.

4. 1-(2-Hydroxyethyl)-5-(2-methyl-3-pyridinyl)-1H-pyrazolo[3,4-b]pyridine, using α-(2-methyl-3-pyridinyl)-β-dimethylaminoacrolein and 5-amino-1-(2-hydroxyethyl)-1H-pyrazole.

5. 5-(3-Ethyl-4-pyridinyl)-1,3-dimethyl-1H-pyrazolo[3,4-b]pyridine, using α-(3-ethyl-4-pyridinyl)-β-dimethylaminoacrolein and 5-amino-1,3-dimethyl-1H-pyrazole.

6. 5-(2,6-Dimethyl-4-pyridinyl)-1-ethyl-1H-pyrazolo[3,4-b]pyridine, using α-(2,6-dimethyl-4-pyridinyl)-β-dimethylaminoacrolein and 5-amino-1-ethyl-1H-pyrazole.

7. 5-(4-Pyridinyl)-1-methyl-1H-pyrazolo[3,4-b]pyridine, using α-(4-pyridinyl)-β-dimethylaminoacrolein and 5-amino-1-methyl-1H-pyrazole.

8. 1-Ethyl-5-(4-pyridinyl)-1H-pyrazolo[3,4-b]pyridine, using α-(4-pyridinyl)-β-dimethylaminoacrolein and 5-amino-1-ethyl-1H-pyrazole.

9. 1-Ethyl-3-methyl-5-(4-pyridinyl)-1H-pyrazolo[3,4-b]pyridine, using α-(4-pyridinyl)-β-dimethylaminoacrolein and 1-ethyl-3-methyl-1H-pyrazole.

10. 1-n-Propyl-5-(4-pyridinyl)-1H-pyrazolo[3,4-b]pyridine, using α-(4-pyridinyl)-β-dimethylaminoacrolein and 5-amino-1-n-propyl-1H-pyrazole.

11. 1-n-Butyl-5-(4-pyridinyl)-1H-pyrazolo[3,4-b]pyridine, using α-(4-pyridinyl)-β-dimethylaminoacrolein and 5-amino-1-n-butyl-1H-pyrazole.

12. 1-Isobutyl-3-methyl-5-(4-pyridinyl)-1H-pyrazolo[3,4-b]pyridine, using α-(4-pyridinyl)-β-dimethylaminoacrolein and 5-amino-1-isobutyl-3-methyl-1H-pyrazole.

13. 1-Isopentyl-5-(4-pyridinyl)-1H-pyrazolo[3,4-b]pyridine, using α-(4-pyridinyl)-β-dimethylaminoacrolein and 5-amino-1-isopentyl-1H-pyrazole.

14. 1-(2-Hydroxy-1-methylethyl)-5-(4-pyridinyl)-1H-pyrazolo[3,4-b]pyridine, using α-(4-pyridinyl)-β-dimethylaminoacrolein and 5-amino-1-(2-hydroxy-1-methylethyl)-1H-pyrazole.

15. 1-(2-Hydroxy-2-methylethyl)-5-(4-pyridinyl)-1H-pyrazolo[3,4-b]pyridine, using α-(4-pyridinyl)-β-dimethylaminoacrolein and 5-amino-1-(2-hydroxy-2-methylethyl)-1H-pyrazole.

16. 1-(3-Hydroxypropyl)-5-(4-pyridinyl)-1H-pyrazolo[3,4-b]pyridine, using α-(4-pyridinyl)-β-dimethylaminoacrolein and 5-amino-1-(3-hydroxypropyl)-1H-pyrazole.

The usefulness of the compound of formula I, or pharmaceutically acceptable acid-addition salt thereof, as a cardiotonic agent is demonstrated by its effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated guinea pig atria and papillary muscle procedure, the compounds of formula I or pharmaceutically acceptable acid-addition salts thereof at doses of 10, 30, 100 μg./ml., were found to cause significant increases, that is, greater than 30% in papillary muscle force and significant increases, that is, greater than 30%, in right atrial force, while causing a lower percentage increase (about one-third or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity of the guinea pig test is designated with a papillary muscle force or right atrial force increase of 31% or greater. For example, when tested at said dose levels by this procedure, the following preferred compound of Example 1, namely 1-(2-hydroxyethyl)-5-(4-pyridinyl)-1H-pyrazolo[3,4-b]pyridine was found to cause respective increases in papillary muscle force and right atrial force of 34% and 22% at 10 µg/ml., 69% and 73% at 30 µg/ml. and 127% and 231% at 100 µg/ml.

The present invention includes within its scope a cardiotonic composition for increasing cardiac contractility, said composition comprising a pharmaceutically acceptable carrier and, as the active component thereof, the cardiotonic 1-R-3-R'-5-PY-1H-pyrazolo[3,4-b]pyridine (formula I) or pharmaceutically acceptable acid-addition salt thereof. The invention also includes within its scope the method for increasing cardiac contractility in a patient requiring such treatment which comprises administering to such patient a cardiotonically effective amount of said 1-R-3-R'-5-PY-1H-pyrazolo[3,4-b]pyridine (formula I) or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

They can be sterilized, for example by filtration through a bacteria-retaining filter, by incorporation of sterilizing agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 1-R-3-R'-5-PY-1H-pyrazolo[3,4-b]pyridine having the formula

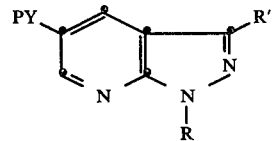

where R is lower-alkyl or lower-hydroxyalkyl, R' is hydrogen or lower-alkyl, and PY is 4- or 3-pyridinyl or 4- or 3-pyridinyl having one or two lower-alkyl substituents, or acid-addition salts thereof.

2. A compound according to claim 1 where R is methyl, ethyl or 2-hydroxyethyl and R' is hydrogen or methyl.

3. A compound according to claim 1 where PY is 4-pyridinyl or 3-pyridinyl.

4. 1(2-Hydroxyethyl)-5-(4-pyridinyl)-1H-pyrazolo[3,4-b]pyridine or acid-addition salt thereof.

5. A cardiotonic composition for increasing cardiac contractility, said composition comprising a pharmaceutically acceptable inert carrier and, as the active component thereof, a cardiotonically effective amount of 1-R-3-R'-5-PY-1H-pyrazolo[3,4-b]pyridine or pharmaceutically acceptable acid-addition salt thereof, where R is lower-alkyl or lower-hydroxyalkyl, R' is hydrogen or lower-alkyl, and PY is 4- or 3-pyridinyl or 4- or 3-pyridinyl having one or two lower-alkyl substituents.

6. A composition according to claim 5 where the active component is 1-(2-hydroxyethyl)-5-(4-pyridinyl)-1H-pyrazolo[3,4-b]pyridine or pharmaceutically acceptable acid-addition salt thereof.

7. The method for increasing cardiac contractility in a patient requiring such treatment which comprises administering orally or parenterally in a solid or liquid dosage form to such patient a cardiotonically effective amount of 1-R-3-R'-PY-1H-pyrazolo[3,4-b]pyridine or pharmaceutically acceptable acid-addition salt thereof, where R is lower-alkyl or lower-hydroxyalkyl, R' is hydrogen or lower-alkyl, and PY is 4- or 3-pyridinyl or 4- or 3-pyridinyl having one or two lower-alkyl substituents.

8. The method according to claim 7 where the cardiotonically active component is 1-(2-hydroxyethyl)-5-(4-pyridinyl)-1H-pyrazolo[3,4-b]pyridine or pharmaceutically acceptable acid-addition salt thereof.

* * * * *